United States Patent [19]

Lieb

[11] Patent Number: 4,519,779
[45] Date of Patent: May 28, 1985

[54] ORTHODONTAL ELECTRICAL DEVICE AND METHOD OF EMPLOYING SAME

[75] Inventor: Nathaniel H. Lieb, Narberth, Pa.

[73] Assignee: Penn-Med Technology, Inc., West Conshohocken, Pa.

[21] Appl. No.: 595,096

[22] Filed: Mar. 30, 1984

[51] Int. Cl.³ .............................................. A61C 7/00
[52] U.S. Cl. ........................................ 433/18; 433/24
[58] Field of Search ................. 433/18, 24; 128/419 F

[56] References Cited

U.S. PATENT DOCUMENTS 4,153,060  5/1979  Korostoff ........................ 128/419 F Primary Examiner—Robert Peshock
Attorney, Agent, or Firm—Caesar, Rivise, Bernstein & Cohen

[57] ABSTRACT

An orthodontal electrical device for assisting in the repositioning of a tooth in the mouth of a patient is attached directly to the tooth to be repositioned to thereby cause anodic and cathodic electrodes thereof to move automatically relative to the gingival lining as the tooth is being repositioned to thereby continuously maintain the desired orientation between the tooth being repositioned and the anodic and cathodic electrodes of the device. The method of employing low current electrical energy to assist in the repositioning of a tooth by automatically moving anodic and cathodic surface electrodes with the movement of the tooth undergoing repositioning also forms a part of the invention.

5 Claims, 7 Drawing Figures

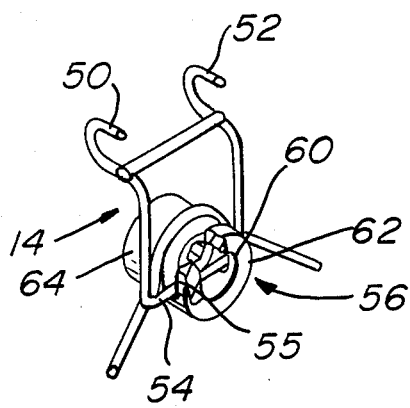
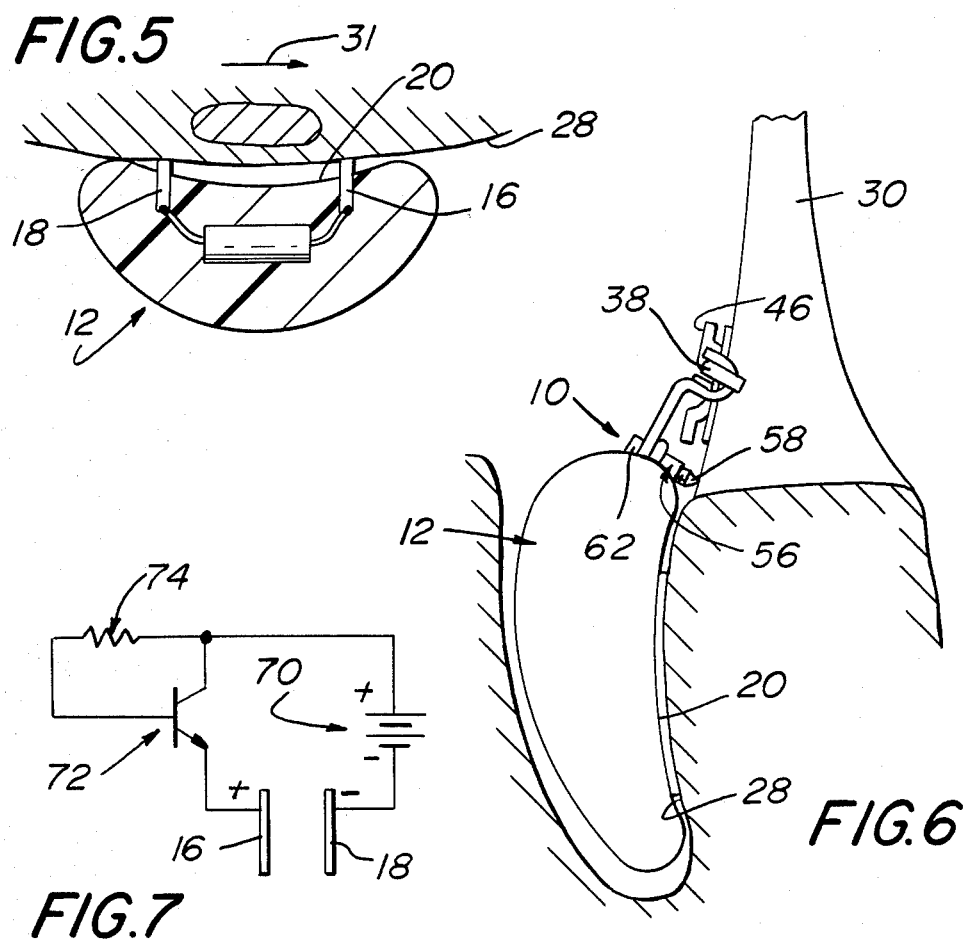

4,519,779

ORTHODONTAL ELECTRICAL DEVICE AND METHOD OF EMPLOYING SAME

BACKGROUND OF THE INVENTION

This invention relates generally to an orthodontal device and method, and more specifically to an orthodontal electrical device and method of employing said device to assist in the repositioning of a tooth in the mouth of a patient.

Research work relating to the use of low amperage current to enhance tooth movement has been carried out at the University of Pennsylvania in Philadelphia, Pa. Early work in this area resulted in the issuance of U.S. Pat. No. 4,153,060 to Korostoff et al.

The Korostoff et al patent discloses a device employing a power pack 28 contained on a base plate 10 that, in turn, is located in the roof of a patient's mouth. The base plate is retained in proper position by fixing it to teeth which are not then being moved with the aid of electrical stimulation.

In the Korostoff et al device the anodic electrode 22 and the cathodic electrode 24 are connected to the positive and negative leads, respectively, of the power pack 28 and are positioned in engagement with the gingival tissue 26. The anodic electrode is placed adjacent the tooth in the direction of desired tooth movement, and the cathodic electrode 24 is placed on the opposite side of the tooth.

When using the Korostoff et al device the anodic and cathodic electrodes will remain in the same location on the gingival tissue as a tooth is undergoing movement, until such time as the position of the electrodes is independently readjusted by the dentist. This is due to the fact that the electrodes are held in a stationary, fixed position on the gingival tissue by virtue of their attachment to a power pack that is located in a fixed position of the patient's mouth. Thus, it is entirely possible that during certain phases of tooth movement the electrodes will not be in an optimum position relative to the tooth to affect the desired degree of tooth movement.

In U.S. Pat. No. 4,244,373, issued to Nachman, devices are disclosed for producing an electrical current in the mouth of a patient. In certain disclosed embodiments, devices are clamped around the teeth to provide electrical stimulation inducing osteogenesis, and possibly to provide increased healing rates for gingival infections. These devices are not employed or designed to assist in effecting tooth movement in accordance with the objectives of the instant invention.

OBJECTS OF THE INVENTION

It is a general object of this invention to enhance tooth movement through the use of low amperage current in a more effective manner than has been accomplished heretofor.

It is a more specific object of this invention to enhance tooth movement by the use of anodic and cathodic electrodes that are moveable relative to the gingival tissue in response to the movement of a tooth being repositioned.

SUMMARY OF THE INVENTION

The above and other objects of this invention are achieved with an orthodontal electrical device utilized to assist in the repositioning of a tooth in the mouth of a patient. The device includes a housing attachable to a tooth to be repositioned, and current, generating means are retained within this housing. An anodic electrode and a cathodic electrode are connected to the appropriate outputs of the current generating means and are located adjacent a surface of the housing facing the gingival tissue when the housing is attached to the tooth to be moved. The anodic electrode is positioned for engaging the gingival tissue adjacent the tooth in a location generally corresponding to the direction in which the tooth is to be repositioned. The cathodic electrode likewise is positioned for engaging the gingival tissue adjacent the tooth, but in a location opposed to the location of the anodic electrode. The method of automatically moving the device in response to the movement of the tooth being repositioned also constitutes a part of this invention.

Other objects and many of the attendant advantages of this invention will be readily appreciated as the same becomes better understood by reference to the following detailed description when considered in connection with the accompanying drawings.

BRIEF DESCRIPTION OF THE DRAWINGS

FIG. 4 is an enlarged front elevational view showing the device of FIG. 1 secured to a tooth to be repositioned in the mouth of an orthodontic patient;

FIG. 5 is a sectional view taken along line 5—5 of FIG. 4;

FIG. 6 is a side elevational view taken along line 6—6 of FIG. 4; and

FIG. 7 is a schematic diagram of the circuitry utilizable in the device of this invention.

DESCRIPTION OF THE BEST MODE FOR CARRYING OUT THE PRESENT INVENTION

Figure 1:
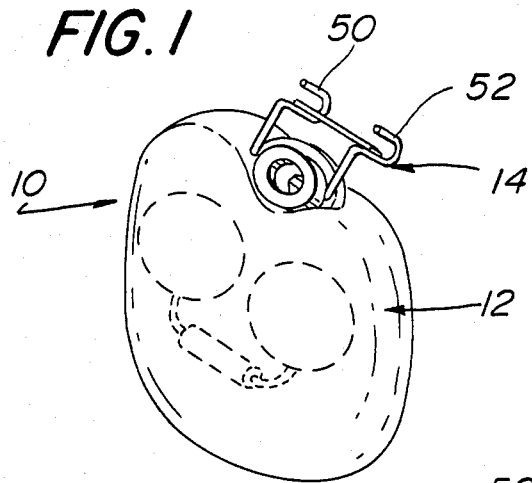
FIG. 1 is an enlarged isometric view of the orthodontic electrical device of this invention.

Referring now in greater detail to the various figures of the drawings wherein like reference characters refer to like parts, an orthodontal electrical device embodying the present invention is generally shown at 10 in FIG. 1. The device 10 also embodies features that constitute the joint invention of John Tlush and Dr. Robert Sanford. These latter features will be identified hereinafter, and also will be covered in a patent application to be filed subsequently. However, the device 10 embodying the inventive features of Mr. John Tlush and Dr. Robert Sanford is disclosed herein because it represents the best mode presently tested for carrying out applicant's invention.

Figure 2:
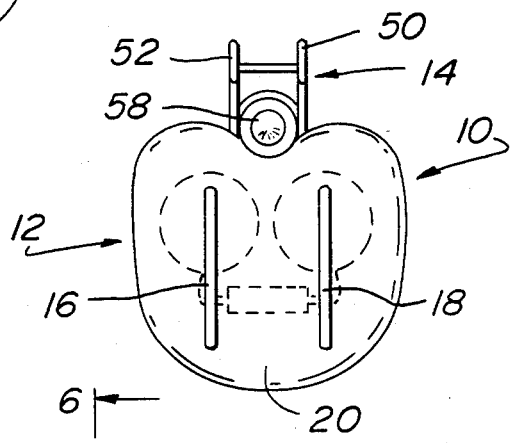
FIG. 2 is a rear elevational view of the device shown in FIG. 1.

Referring specifically to FIGS. 1 and 2, the orthodontal electrical device 10 includes a housing 12 preferably molded of a suitable acrylic material to a clip assembly 14. Circuit generating current means are disposed within the housing, and are connected to an anodic electrode 16 and a cathodic electrode 18 located adjacent the rear surface 20 of said housing. It is within the scope of the invention to embed a portion of the anodic and cathodic electrodes in the acrylic housing; however, at least a part of each of these electrodes must be exposed for engaging the gingival tissues 28 to accomplish the objectives of the present invention.

Referring specifically to FIGS. 4–6, the orthodontal electrical device 10 is shown attached to a patient's tooth 30 to be repositioned; with the housing 12 of said device being opposed to the gingival tissue 28 adjacent said tooth. As can be seen best in FIG. 5, arrow 31 indicates the direction in which the tooth 30 is to be repositioned, and shows the anodic electrode 16 in its desired position engaging the gingival tissue 28 in the general direction of tooth movement. The cathodic electrode 18 likewise is positioned in engagement with the gingival tissue 28, but on the side of the tooth 30 opposed to the direction of desired tooth movement.

The general principles embodied in the present invention for repositioning teeth are the same as those described by Korostoff et al in U.S. Pat. No. 4,153,060. The subject matter of the Korostoff et al patent is herein incorporated by reference.

Referring specifically to FIG. 4 the orthodontal device 10 is removably attached to the tooth 30 through a unique orthodontic bracket arrangement 32 which was invented jointly by Mr. John Tlush and Dr. Robert Sanford. This bracket arrangement includes an orthodontic bracket 34 which is bonded in a conventional manner to the tooth 30 with a conventional orthodontic cement. This bracket 34 includes a conventional groove 36 for receiving an arch wire employed to assist in the movement and/or alignment of a patient's teeth. The bracket 34 also is provided with a unique arrangement of laterally aligned passages 40 and 42 in uniquely designed upper head sections 44 and 46 to receive an orthodontic wire 38 therein. It is to this orthodontic wire 38 that the orthodontal device 10 is removably attached.

Figure 3:
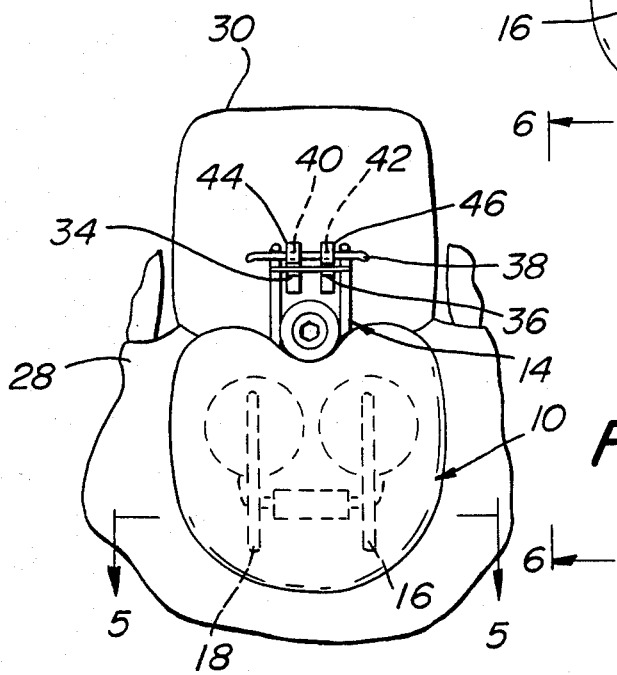
FIG. 3 is an enlarged isometric view of the clip assembly forming a part of the device illustrated in FIG. 1.

As can be seen best in FIGS. 3 and 4, the clip assembly 14 is employed to attach the device 10 to the bracket 32. This clip assembly 14 also constitutes the joint invention of Mr. John Tlush and Dr. Robert Sanford.

The embodiment of the invention contemplated by applicant herein is to bond the device with a conventional orthodontal cement to a patient's tooth with the electrodes of said device located in proper position on the gingival tissue. In accordance with applicant's embodiments the device can be bonded directly to the tooth surface or to an orthodontic appliance fastened to, and moveable with said tooth.

Still referring to FIGS. 3 and 4 the clip assembly 14 includes a generally U-shaped clip 15 having generally U-shaped hooks 50 and 52 at the ends of laterally spaced-apart legs thereof. It is these hooks that are received about the orthodontic wire 38 to removably secure the device 10 to the tooth 30, as can be seen best in FIGS. 4 and 6.

The clip 15 further includes a base element 54 which is welded into the base of slot 55 of a modified gurin lock 56 of the assembly 14.

Referring to FIGS. 3 and 6, the modified gurin lock 56 can be formed from a conventional gurin lock by turning the locking pin 58 so that its pointed end faces outwardly, rather than inwardly toward slot 55, as can be seen best in FIG. 6. In this position the pointed end of the pin 58 is employed to press against the tooth 30 for the purpose of assisting in establishing the desired spacing of the housing 12 and the associated electrodes 16 and 18 relative to the gingival tissue 28. In order to provide access to the head of the locking pin 58 for the purpose of permitting its adjustment, a passageway 60 (FIG. 3) is formed through segment 62 of the housing of the lock opposed to segment 64 in which the locking pin 58 is threaded.

As can be seen best in FIG. 3 the clip assembly 14 further includes a housing-attachment wire 62 welded to the body of the lock 56. The ends of this wire are embedded within the molded acrylic housing 12 to form the completed device 10.

Referring to FIG. 7, a representative current generating circuit means employed in the device 10 is illustrated. In the illustrated embodiment the power source is located at 70, and is provided by four, 1½ volt silver oxide batteries of the general type employed in hearing aids. This power source is connected through a suitable transistor 72 and resistor 74 to provide the desired low amperage output connectable to the anodic electrode 16 and the cathodic electrode 18. In one embodiment the low current amperage is on the order of 21 microamperes; however, the specific amperage may vary depending upon the particular patient being treated and the particular rate of tooth movement desired.

Without further elaboration the foregoing will so fully illustrate my invention that others may, by applying current or future knowledge, adopt the same for use under various conditions of service.

I claim:

1. An orthodontal electrical device for assisting in the repositioning of a tooth in the mouth of a patient, said device being characterized by:
    a. a housing attachable to a tooth to be repositioned and moveable with said tooth;
    b. current generating means within said housing;
    c. an anodic electrode connected to said current generating means and being moveable with said housing, said anodic electrode being located adjacent a surface of the housing facing the gingival tissue when said housing is attached to the tooth to be repositioned, said anodic electrode being positioned for engaging the gingival tissue adjacent the tooth to be repositioned for engaging the gingival tissue adjacent the tooth to be repositioned at a location substantially in a direction of desired tooth movement; and
    d. a cathodic electrode connected to said circuit generating means and being moveable with said housing, said cathodic electrode being located adjacent the same surface of the housing as the anodic electrode and bing positioned for engaging the gingival tissue adjacent the tooth to be repositioned on the side of said tooth opposed to the anodic electrode.

2. The device of claim 1 characterized in that the housing is attached to the tooth through an orthodontic appliance that, in turn, is attached to the tooth to be repositioned and that is moveable with said tooth to be repositioned.

3. The device of claim 1 characterized in that the housing is attachable to the tooth by a bonding material.

4. A method of repositioning a tooth in the mouth of a patient comprising the steps of:
    a. positioning an anodic electrode adjacent said tooth to be repositioned at a location towards which repositioning is desired;
    b. applying a cathodic electrode adjacent said tooth to be repositioned at a location opposed to said anodic electrode;
    c. causing a current to flow between said anodic and cathodic electrodes to assist in repositioning the tooth; and d. automatically moving the anodic electrode and cathodic electrode with the tooth being repositioned to thereby continuously maintain the desired relative position between the tooth being repositioned and said anodic and cathodic electrodes.

5. The method of claim 4 characterized in that the automatic movement is achieved by securing a device including the anodic and cathodic electrodes to the tooth undergoing repositioning.

* * * * *